(12) United States Patent
Yanagihara et al.

(10) Patent No.: US 7,547,280 B2
(45) Date of Patent: Jun. 16, 2009

(54) SYSTEM AND METHOD FOR COMMUNICATING BIOLOGICAL SIGNAL DATA

(75) Inventors: Kazuteru Yanagihara, Tokyo (JP); Takahisa Ishikawa, Tokyo (JP); Kenta Sudo, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 0 days.

(21) Appl. No.: 10/995,330

(22) Filed: Nov. 24, 2004

(65) Prior Publication Data

US 2005/0119535 A1 Jun. 2, 2005

(30) Foreign Application Priority Data

Nov. 27, 2003 (JP) ............................ P2003-396966

(51) Int. Cl.
*A61B 5/00* (2006.01)
(52) U.S. Cl. ...................................... 600/300; 128/920
(58) Field of Classification Search ......... 600/300–301, 600/509; 128/903–905; 714/749; 340/539.12
See application file for complete search history.

(56) References Cited

U.S. PATENT DOCUMENTS 5,623,934 A 4/1997 Midorikawa
5,699,367 A * 12/1997 Haartsen .................... 714/749
5,748,103 A * 5/1998 Flach et al. ................. 600/509

FOREIGN PATENT DOCUMENTS

| JP | 2000-232964 A | 8/2000 |
| JP | 3220737 B2 | 8/2001 |
| JP | 2002-541893 A | 12/2002 |
| JP | 2003-168178 A | 6/2003 |

* cited by examiner

*Primary Examiner*—Michael C Astorino
(74) *Attorney, Agent, or Firm*—Sughrue Mion, PLLC

(57) ABSTRACT

A measurement apparatus and a receiver apparatus are communicatively connected in a wireless manner. Biological signal data is obtained from a detector attached on a living body. A data packet is prepared from the biological signal data. A first CRC of the biological signal data is calculated and appended to the data packet. The data packet is periodically transmitted with the first CRC from the measurement apparatus to the receiver apparatus. A second CRC of the data packet received at the receiver apparatus is calculated. The received data packet is verified when the second CRC is coincident with the first CRC. Acknowledgement data is transmitted from the receiver apparatus to the measurement apparatus when the received data packet is verified. The data packet is retransmitted from the measurement apparatus to the receiver apparatus when the acknowledgement data is not received at the measurement apparatus within a prescribed time period from a previous transmission of the data packet. The data packet is stored in a storage when the number of retransmission exceeds a prescribed value.

11 Claims, 3 Drawing Sheets

FIG. 3A

| FC | LENGTH | TYPE | SN | DSTID | SRCID | PAYLOAD | FCS |
|---|---|---|---|---|---|---|---|
| 2BYTE | 2BYTE | 2BYTE | 2BYTE | 4BYTE | 4BYTE | 1536BYTE ~ 512BYTE | 4BYTE |

FIG. 3B

| FC | LENGTH | TYPE | SN | DSTID | SRCID | FCS |
|---|---|---|---|---|---|---|
| 2BYTE | 2BYTE | 2BYTE | 2BYTE | 4BYTE | 4BYTE | 4BYTE |

SYSTEM AND METHOD FOR COMMUNICATING BIOLOGICAL SIGNAL DATA

BACKGROUND OF THE INVENTION

The present invention relates to a system and a method for transmitting biological signal data measured by a biological signal measurement apparatus to a receiver apparatus located remote from the biological signal measurement apparatus.

In order to cause biological signal data, which have been measured by a biological signal measurement apparatus such as an electroencephalograph (hereinafter, simply referred as "measurement apparatus") attached on a patient, to be displayed or transmitted to a receiver apparatus for analysis, the measurement apparatus and the receiver apparatus may be connected by way of a communication cable for wired transmission of the data so that the data can be received in a reliable manner.

However, when the measurement apparatus and the receiver apparatus are connected by way of a communication cable or the like, the patient, being restrained by the communication cable, is prevented from walking around freely.

To solve the problem, there has hitherto been known a method to effect wireless communication of measured data between a measurement apparatus attached on a patient, and a receiver apparatus (cf., Japanese Patent No. 3220737).

As described above, wireless transmission of measured data provides an advantage that a patient who carries a measurement apparatus can walk around freely in a hospital or the like. However, when radio interference occurs or the patient travels to a location which radio waves cannot reach, the receiver apparatus fails to receive the measured data.

Since a conventional measurement apparatus utilizing wireless transmission does not check whether or not transmitted measured data are appropriately received by a receiver apparatus, the measured data are not retransmitted in the event that the receiver apparatus fails to receive the data.

In a case where measured data is transmitted in a wireless manner, when radio interference occurs or the patient travels to a location which radio waves cannot reach, receipt of measurement data by the receiver apparatus is interrupted and the apparatus cannot adequately process the measured data.

SUMMARY OF THE INVENTION

It is therefore an object of the invention to provide a system and a method for communicating biological signal data, wherein it is verified whether the biological signal measured and transmitted from a measurement apparatus is appropriately received by a receiver apparatus, and wherein the biological signal data is easily retransmitted if the receiver apparatus fails to receive the data appropriately.

In order to achieve the above object, according to the invention, there is provided a system for communicating biological signal data, comprising:

at least one measurement apparatus, comprising a detector, adapted to be attached on a living body to obtain the biological signal data; and a receiver apparatus, communicatively connected to the at least one measurement apparatus in a wireless manner, wherein:

the measurement apparatus further comprises:

a storage;

a first communicator, operable to periodically transmit the biological signal data as a data packet to the receiver apparatus, and operable to receive acknowledgement data from the receiver apparatus;

an appender, which calculates a first cyclic redundancy check of the biological signal data and appends the first cyclic redundancy check to the data packet; and a first controller, operable to cause the first communicator to retransmit the data packet when the first communicator does not receive the acknowledgement data within a prescribed time period from a previous transmission of the data packet, and operable to store the data packet in the storage when the number of retransmission exceeds a prescribed value; and the receiver apparatus further comprises:

a second communicator, operable to receive the data packet from the measurement apparatus, and operable to transmit the acknowledgement data to the measurement apparatus;

a verifier, which calculates a second cyclic redundancy check of the data packet received by the second communicator and verifies the data packet when the second calculated cyclic redundancy check is coincident with the first cyclic redundancy check; and a second controller, operable to cause the second communicator to transmit the acknowledgement data to the measurement apparatus when the data packet is verified.

With the above configuration, even when radio interference occurs or the living body (patient) travels to a location which radio waves cannot reach, the receiver apparatus can be prevented from failing to receive the biological signal data.

Preferably, the first controller causes the first communicator to periodically confirm whether the data communication between the measurement apparatus and the receiver apparatus is possible. The retransmission is performed in a condition that it is confirmed that the data communication is possible.

Preferably, the measurement apparatus is configured to measure at least one of electroencephalogram, electrocardiogram, electromyogram, respiration waveform and oxygen saturation in arterial blood.

According to the invention, there is also provided a method for communicating biological signal data between a measurement apparatus and a receiver apparatus which are communicatively connected in a wireless manner, the method comprising steps of:

obtaining the biological signal data from a detector attached on a living body;

preparing a data packet from the biological signal data;

calculating a first cyclic redundancy check of the biological signal data;

appending the first cyclic redundancy check to the data packet;

transmitting periodically the data packet with the first cyclic redundancy check from the measurement apparatus to the receiver apparatus;

receiving the data packet at the receiver apparatus;

calculating a second cyclic redundancy check of the received data packet;

verifying the received data packet when the second cyclic redundancy check is coincident with the first cyclic redundancy check;

transmitting acknowledgement data from the receiver apparatus to the measurement apparatus when the received data packet is verified;

retransmitting the data packet from the measurement apparatus to the receiver apparatus when the acknowledgement data is not received at the measurement apparatus within a prescribed time period from a previous transmission of the data packet; and storing the data packet in a storage when the number of retransmission exceeds a prescribed value.

Preferably, it is performed a step of confirming periodically whether the data communication between the measurement apparatus and the receiver apparatus is possible. The retransmission is performed in a condition that it is confirmed that the data communication is possible.

Preferably, an amount of data transmitted within a unit time period in the retransmission is greater than an amount of data transmitted within the unit time period in the periodic transmission.

According to the invention, there is provided a measurement apparatus, communicatively connected to a receiver apparatus in a wireless manner, comprising:

a detector, adapted to be attached on a living body to obtain biological signal data;

a storage;

a communicator, operable to periodically transmit the biological signal data as a data packet to the receiver apparatus, and operable to receive acknowledgement data from the receiver apparatus;

an appender, which calculates a cyclic redundancy check of the biological signal data and appends the cyclic redundancy check to the data packet; and a controller, operable to cause the first communicator to retransmit the data packet when the first communicator does not receive the acknowledgement data within a prescribed time period from a previous transmission of the data packet, and operable to store the data packet in the storage when the number of retransmissions exceeds a prescribed value.

According to the invention, there is also provided a receiver apparatus, communicatively connected to at least one measurement apparatus in a wireless manner, the measurement apparatus being configured to periodically transmit biological signal data as a data packet with a first cyclic redundancy check. The receiver apparatus comprises:

a communicator, operable to receive the data packet from the measurement apparatus, and operable to transmit acknowledgement data to the measurement apparatus;

a verifier, which calculates a second cyclic redundancy check of the data packet received by the communicator and verifies the data packet when the second calculated cyclic redundancy check is coincident with the first cyclic redundancy check; and a controller, operable to cause the communicator to transmit the acknowledgement data to the measurement apparatus when the data packet received by the communicator is verified.

According to the invention, it is enabled receipt of accurate biological signal data without interruption even when radio interference of a telemetry circuit occurs or when a patient carrying the measurement apparatus travels to a location which radio waves cannot reach. Therefore, the invention can be effectively applied to the epilepsy monitoring or the polysomnogram, whose pathological signs are expressed at unpredictable times.

Additionally, in the case when pathological signs are expressed, failure to capture measured data of electroencephalogram measurement is prevented, thereby enabling more accurate analysis and diagnosis. Therefore, the invention is useful for discovering a point where epilepsy, abnormal electroencephalograms, or the like have arisen, as well as treatment of the epilepsy, abnormal electroencephalograms, or the like.

BRIEF DESCRIPTION OF THE DRAWINGS

The above objects and advantages of the present invention will become more apparent by describing in detail preferred exemplary embodiments thereof with reference to the accompanying drawings, wherein:

FIGS. 3A and 3B are diagrams showing data formats for use in data communication in the system of FIG. 1.

DETAILED DESCRIPTION OF THE INVENTION

One embodiment of the invention will be described below in detail with reference to the accompanying drawings.

Figure 1:
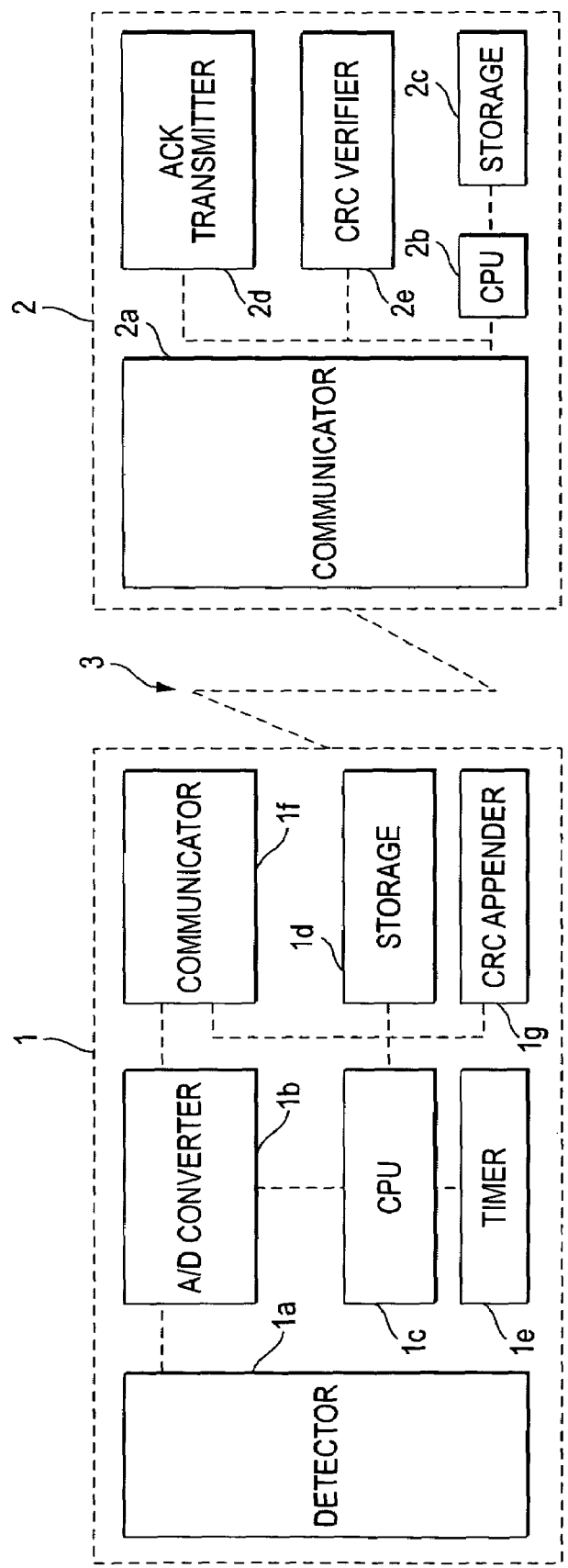
FIG. 1 is a block diagram showing a system for communicating biological signal data according to one embodiment of the invention.

As shown in FIG. 1, a measurement apparatus 1 adapted to be attached on or carried by a patient to measure biological system thereof and a receiver apparatus 2 are connected by way of a telemetry circuit 3 to constitute a communication system of the invention.

The measurement apparatus 1 comprises: a detector (e.g., an electrode) 1a adapted to be attached on an unillustrated subject (living body) for detecting a biological signal of the subject (e.g., electroencephalogram); an A/D converter 1b for effecting analog-to-digital conversion of the detected biological signal; a CPU 1c; a storage 1d; a timer 1e; a communicator 1f; and a CRC (cyclic redundancy check) appender 1g.

The receiver apparatus 2 comprises: a communicator 2a; a CPU 2b; a storage 2c; an ACK transmitter 2d; and a CRC verifier 2e.

An electroencephalogram signal detected from the detector 1a (electrodes) attached on a head of the unillustrated subject is converted into a digital signal in the AD converter 1b, and stored in the storage 1d contiguously.

The CPU 1c transmits the thus-stored measured data periodically as a data packet to the receiver apparatus 2 by way of the communicator 1f at a timing prescribed by the timer 1e (e.g., every 10 seconds).

At the time of periodic transmission of measurement data measured by the detector 1a (e.g., electroencephalogram data in the case where the detector 1a is an electroencephalograph) to the receiver apparatus 2, the measurement apparatus 1 causes the CRC appender 1g to calculate a CRC for error detection and to append the thus-calculated CRC into a transmission data packet, which will be described later.

The receiver apparatus 2 calculates a CRC of the data packet received by the CPU 2b, and compares the calculated CRC with the CRC received by way of the communicator 2a, thereby verifying consistency of the received data.

When the received data are determined to contain no errors through verification, an acknowledgment packet (hereinafter referred to as "ACK") is prepared by the ACK transmitter 2d and returned to the communicator 1f of the measurement apparatus 1.

However, when receipt of accurate data is failed by occurrence of radio interference, such as crosstalk or interference, in the telemetry circuit 3, the verification result reveals that the CRC values are not identical. At this time, the ACK is not returned.

Additionally, when the patient carrying the measurement apparatus 1 travels to a location which the radio waves cannot reach, the receiver apparatus 2 cannot receive correct data. Accordingly, the ACK is not returned, as is the case with the above.

When the communicator 1f of the measurement apparatus 1 receives the ACK, transmission of the data packet is assumed to be completed.

In the case where the measurement apparatus 1 cannot receive the ACK from the receiver apparatus 2 within a prescribed time period after the transmission of the data packet, the transmission error is assumed and the data packet is then retransmitted.

In the case where the ACK is received within the prescribed time period after the retransmission of the data packet, the transmission is assumed to be completed. However, in the case where the ACK cannot be received even after a prescribed number of retransmissions, the state is assumed to be communication-blocked, and subsequent measurement data including the data packet are stored (for backup) in the storage 1d. The storage of the measurement data is to be repeated so long as the ACK cannot be received.

Thereafter, the communicator 1f of the measurement apparatus 1 periodically checks the communication state with the receiver apparatus 2. When communication becomes possible, transmission of the stored backup data is resumed.

Communication state is ascertained on the basis of whether or not correct response data is returned when ascertainment data are transmitted periodically (e.g., every one second) from the measurement apparatus 1 to the receiver apparatus 2.

The storage 1d preferably has a capacity of storing data in an amount corresponding to measurement data of one hour or longer.

Further, with regard to transmission of the stored measurement data, measured data in an amount of 10 or more times that of a normal transmission are preferably transmitted within a unit time period. For example, such a transmission can be achieved by increasing the amount of data contained in a payload portion of the data packet (described later), or by shortening intervals between the periodic transmissions of the packet.

Figure 2:
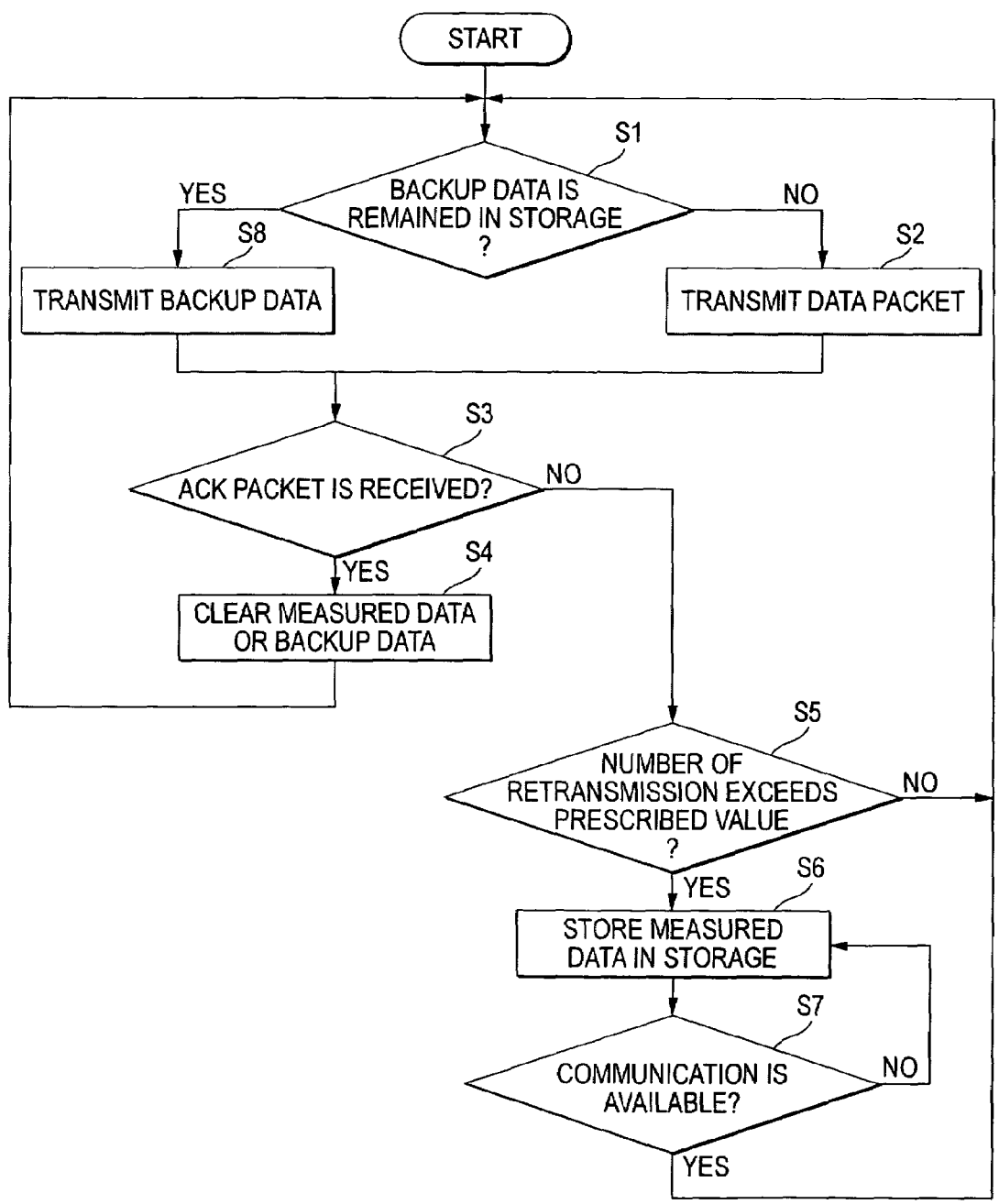
FIG. 2 is a flow chart showing operations performed in a measurement apparatus in the system of FIG. 1.

Of the above data flow between the measurement apparatus 1 and the receiver apparatus 2, operations in the measurement apparatus 1 will be described with reference to a flow chart shown in FIG. 2.

At the beginning of the operations, a determination is made as to whether or not backup data is still stored in the storage 1d (step S1).

If the result of the determination made in step S1 is NO, a CRC for error detection is calculated; and the transmission data packet including the measurement data, and the calculated CRC is transmitted (step S2).

If the result of the determination made in step S1 is YES, a CRC for error detection is calculated; and the data packet including the backup data, and the calculated CRC is transmitted (step S8).

A determination is made as to whether or not an ACK packet from the receiver apparatus 2 is received within the prescribed time period after transmission of the data packet at step S2 or S8 (step S3).

If the result of the determination made in step S3 is YES, it is judged that the data are transmitted normally; transmitted measurement data or transmitted backup data are cleared (step S4); and processing returns to step S1.

If the result of the determination made in step S3 is NO, a determination is made as to whether or not the number of times of retransmissions has exceeded the prescribed value (step S5).

If the result of the determination made in step S5 is NO, processing returns to step S1 (i.e., retransmission of the data packet).

If the result of the determination made in step S5 is YES, the packet data and data scheduled to be transmitted thereafter are stored in the storage 1d (for backup) (step S6).

Thereafter, a determination is periodically made as to whether or not communication with the receiver apparatus 2 is possible (step S7).

If the result of the determination made in step S7 is YES, processing returns to step $S_1$, and retransmission of the backup data stored in the storage 1d is resumed.

If the result of the determination made in step S7 is NO, processing returns to step S6, so that the backup data is still stored in the storage 1d.

Next, an example data format for communicating measurement data employed in the invention will be described with reference to FIGS. 3A and 3B.

FIG. 3A shows a packet format of a data packet to be transmitted from the measurement apparatus 1 to the receiver apparatus 2.

The packet format comprises a 2-byte frame control (FC), a 2-byte data length (Length), a 2-byte data type (Type), a 2-byte sequence number (SN), a 4-byte destination radio ID (DstID), a 4-byte source ID (SrcID), a data of 1536 to 512 bytes (Payload), and a 4-byte frame check sequence (FCS). More specifically, "Length" defines the data length from "TYPE" to "Payload".

Further, as shown in FIG. 3B, a packet format of an ACK packet to be transmitted from the receiver apparatus 2 to the measurement apparatus 1 comprises a 2-byte frame control (FC), a 2-byte data length (Length), a 2-byte data type (Type), a 2-byte sequence number (SN), a 4-byte destination radio ID (DstID), a 4-byte source ID (SrcID), and a 4-byte frame check sequence (FCS). More specifically, "Length" defines the data length from "TYPE" to "SrcID".

With the above configuration, accurate measurement data is received without interruption even when radio interference of the telemetry circuit 3 occurs or the patient carrying the measurement apparatus travels to a location which radio waves cannot reach. Therefore, the data communication system can be applied to the epilepsy monitoring or the polysomnogram, whose pathological signs are expressed at unpredictable times.

Additionally, in the case when pathological signs are expressed, failure to capture measured data of electroencephalogram measurement will be prevented, thereby enabling more accurate analysis and diagnosis. Therefore, the data communication system is useful for discovering a point where epilepsy, abnormal electroencephalograms, or the like have arisen, as well as treatment thereof.

Although the present invention has been shown and described with reference to specific preferred embodiments, various changes and modifications will be apparent to those skilled in the art from the teachings herein. Such changes and modifications as are obvious are deemed to come within the spirit, scope and contemplation of the invention as defined in the appended claims.

What is claimed is:

1. A system for communicating biological signal data, comprising:

at least one measurement apparatus, comprising a detector, that is adapted to be attached on a living body to obtain the biological signal data; and a receiver apparatus, communicatively connected to the at least one measurement apparatus in a wireless manner, wherein:

the measurement apparatus further comprises:

a storage;

a first communicator that periodically transmits the biological signal data as a data packet to the receiver apparatus, and that receives acknowledgement data from the receiver apparatus; and an appender that calculates a first cyclic redundancy check of the biological signal data and appends the first cyclic redundancy check to the data packet;

the receiver apparatus comprises:

a second communicator that receives the data packet from the measurement apparatus, and transmits, to the measurement apparatus, acknowledgement data indicative of a receipt of the data packet;

a verifier that calculates a second cyclic redundancy check of one of the data packet received by the second communicator and verifies the data packet when the second calculated cyclic redundancy check is coincident with the first cyclic redundancy check of the data packet; and a first controller that causes the second communicator to transmit the acknowledgement data to the measurement apparatus when the data packet is verified, the measurement apparatus further comprises;

a second controller that causes the first communicator to retransmit the data packet when the first communicator does not receive the acknowledgement data within a prescribed time period from a previous transmission of the data packet, and that checks to determine if the number of transmissions exceed a prescribed value and stores the data packet in the storage when the number of retransmission of the data packet exceeds a prescribed value.

2. The system as set forth in claim 1, wherein:

the second controller causes the first communicator to periodically confirm whether the data communication between the measurement apparatus and the receiver apparatus is possible, in a case where the data packet is stored in the storage;

the second controller stores at least one subsequent data packet corresponding to subsequent biological signal data until it is confirmed that the data communication is possible; and the second controller causes the first communicator to retransmit the data packet stored in the storage when it is confirmed that the data communication is possible, together with the at least one subsequent data packet in a case where the at least one subsequent data packet is stored in the storage.

3. The system as set forth in claim 1, wherein the measurement apparatus is configured to measure at least one of electroencephalogram, electrocardiogram, electromyogram, respiration waveform and oxygen saturation in arterial blood.

4. A method for communicating biological signal data between a measurement apparatus and a receiver apparatus which are communicatively connected in a wireless manner, the method comprising:

obtaining the biological signal data from a detector attached on a living body;

preparing a data packet from the biological signal data;

calculating a first cyclic redundancy check of the biological signal data;

appending the first cyclic redundancy check to the data packet;

transmitting periodically the data packet with the first cyclic redundancy check from the measurement apparatus to the receiver apparatus;

receiving the data packet at the receiver apparatus;

calculating a second cyclic redundancy check of the received data packet;

verifying the received data packet when the second cyclic redundancy check is coincident with the first cyclic redundancy check;

transmitting acknowledgement data from the receiver apparatus to the measurement apparatus when the received data packet is verified;

retransmitting the data packet from the measurement apparatus to the receiver apparatus when the acknowledgement data is not received at the measurement apparatus within a prescribed time period from a previous transmission of the data packet;

checking to determine if the number of transmissions exceed a prescribed value;

storing the data packet in a storage when the number of retransmission of the data packet exceeds a prescribed value.

5. The method as set forth in claim 4, further comprising:

confirming periodically whether the data communication between the measurement apparatus and the receiver apparatus is possible, in a case where the data packet is stored in the storage;

storing at least one subsequent data packet corresponding to subsequent biological signal data until it is confirmed that the data communication is possible; and retransmitting the data packet stored in the storage when it is confirmed that the data communication is possible, together with the at least one subsequent data packet in a case where the at least one subsequent data packet is stored in the storage.

6. A measurement apparatus, communicatively connected to a receiver apparatus in a wireless manner, comprising:

a detector that is adapted to be attached on a living body to obtain biological signal data;

a storage;

a communicator that periodically transmits the biological signal data as a data packet to the receiver apparatus and that receives, from the receiver apparatus, acknowledgement data indicative of a receipt of the data packet at the receiver apparatus;

an appender that calculates a cyclic redundancy check of the biological signal data and appends the cyclic redundancy check to the data packet; and a controller that causes the communicator to retransmit the data packet when the communicator does not receive the acknowledgement data within a prescribed time period from a previous transmission of the data packet, and stores the data packet in the storage when the number of retransmission of the data packet exceeds a prescribed value.

7. The measurement apparatus as set forth in claim 6, wherein:

the controller causes the communicator to periodically confirm whether the data communication between the measurement apparatus and the receiver apparatus is possible, in a case where the data packet is stored in the storage;

the controller stores at least one subsequent data packet corresponding to subsequent biological signal data until it is confirmed that the data communication is possible; and the controller causes the communicator to retransmit the data packet stored in the storage when it is confirmed that the data communication is possible, together with the at least one subsequent data packet in a case where the at least one subsequent data packet is stored in the storage.

8. A system for communicating biological signal data, comprising:

at least one measurement apparatus, comprising a detector, adapted to be attached on a living body to obtain the biological signal data; and a receiver apparatus, communicatively connected to the at least one measurement apparatus in a wireless manner, wherein:

the measurement apparatus further comprises:
  a storage;
  first communication means for periodically transmitting the biological signal data as a data packet to the receiver apparatus, and for receiving acknowledgement data from the receiver apparatus; and
  first calculation means for calculating a first cyclic redundancy check of the biological signal data and appends the first cyclic redundancy check to the data packet;

the receiver apparatus comprises:
  second communication means for receiving the data packet from the measurement apparatus, and for transmitting, to the measurement apparatus, acknowledgement data indicative of a receipt of the data packet;
  second calculation means for calculating a second cyclic redundancy check of one of the data packet received by the second communication means to verify the data packet when the second calculated cyclic redundancy check is coincident with the first cyclic redundancy check of the data packet; and
  first control means for causing the second communication means to transmit the acknowledgement data to the measurement apparatus when the data packet is verified, the measurement apparatus further comprises:
  second control means for causing the first communication means to retransmit the data packet when the first communication means does not receive the acknowledgement data within a prescribed time period from a previous transmission of the one of the data packets, and for checking to determine if the number of transmissions exceed a prescribed value and for storing the data packet in the storage when the number of retransmission of the data packet exceeds a prescribed value.

9. The system as set forth in claim 8, wherein:
the second control means causes the first communication means to periodically confirm whether the data communication between the measurement apparatus and the receiver apparatus is possible, in a case where the data packet is stored in the storage;

the second control means stores at least one subsequent data packet corresponding to subsequent biological signal data until it is confirmed that the data communication is possible; and the second control means causes the first communication means to retransmit the data packet stored in the storage when it is confirmed that the data communication is possible, together with the at least one subsequent data packet in a case where the at least one subsequent data packet is stored in the storage.

10. A measurement apparatus, communicatively connected to a receiver apparatus in a wireless manner, comprising:

a detector, adapted to be attached on a living body to obtain biological signal data;

a storage;

communication means for periodically transmitting the biological signal data as a data packet to the receiver apparatus, and for receiving, from the receiver apparatus, acknowledgement data indicative of a receipt of the data packet at the receiver apparatus;

calculation means for calculating a cyclic redundancy check of the biological signal data and appends the cyclic redundancy check to the data packet; and control means for causing the communication means to retransmit the data packet when the communication means does not receive the acknowledgement data within a prescribed time period from a previous transmission of the data packet, and for checking to determine if the number of transmissions exceed a prescribed value and storing the data packet in the storage when the number of retransmission of the data packet exceeds a prescribed value.

11. The measurement apparatus as set forth in claim 10, wherein:
the control means causes the communication means to periodically confirm whether the data communication between the measurement apparatus and the receiver apparatus is possible, in a case where the data packet is stored in the storage;

the control means stores at least one subsequent data packet corresponding to subsequent biological signal data until it is confirmed that the data communication is possible; and the control means causes the communication means to retransmit the data packet stored in the storage when it is confirmed that the data communication is possible, together with the at least one subsequent data packet in a case where the at least one subsequent data packet is stored in the storage.

* * * * *